United States Patent [19]

Wixforth

[11] Patent Number: 5,137,717
[45] Date of Patent: Aug. 11, 1992

[54] COSMETIC PREPARATION HAVING GERMICIDAL PROPERTIES

[76] Inventor: Bruno Wixforth, Wilhelm-Bohmert Str. 17, D-2800 Bremen 33, Fed. Rep. of Germany

[21] Appl. No.: 574,371

[22] Filed: Aug. 29, 1990

Related U.S. Application Data

[63] Continuation of Ser. No. 242,793, Sep. 9, 1988, abandoned.

[30] Foreign Application Priority Data

Sep. 11, 1987 [DE] Fed. Rep. of Germany ....... 3730522

[51] Int. Cl.$^5$ .......................... A61K 9/68; A61K 7/16; A61K 7/32; A01N 25/04
[52] U.S. Cl. .............................. 424/78.07; 424/78.03; 424/48; 424/49; 424/65; 424/69
[58] Field of Search ........................ 424/49, 48, 65, 69, 424/78.03, 78.07

[56] References Cited

FOREIGN PATENT DOCUMENTS 1617556 4/1971 Fed. Rep. of Germany .
2637862 3/1978 Fed. Rep. of Germany .
2133237 10/1972 France .

OTHER PUBLICATIONS

Chemical Abstracts, vol. 40, No. 22, Nov. 20, 1946, "Antibiotic Action of Quinones. I Antibiotic activity against Staphylococcus pygenes aureaus in vitro".
Chemical Abstracts, vol. 89, No. 9, Aug. 8, 1978, "The inhibition of various micro-organisms by crude walnut hull extracts and juglone".
Chemical Abstracts, vol. 76, No. 16, Apr. 17, 1972, "Chemical Extractives from Walnut Bark (Juglans regia) and their effects on the cleansing of tartar deposits."
"Seife-Öle-Fette-Wachse", vol. 107, No. 20, Dec. 1981, pp. 623-625.

*Primary Examiner*—Thurman K. Page
*Assistant Examiner*—C. Azpuru
*Attorney, Agent, or Firm*—Ostrolenk, Faber, Gerb & Soffen

[57] ABSTRACT

A cosmetic preparation having germicidal properties is set forth, which contains 5-hydroxy-1,4-naphthoquinone as such, in the form of plant parts or in the form of a extract obtained from the plant parts. Preferable cosmetic preparations are preparations for oral and dental care, deodorants and a foot powder.

The use of 5-hydroxy-1,4-naphthoquinone as a germicidal agent for cosmetic preparations either as such or in the form of plant parts or an extract obtained from the plant parts is also described.

13 Claims, No Drawings

COSMETIC PREPARATION HAVING GERMICIDAL PROPERTIES

This is a continuation of application Ser. No. 07/242,793, filed on Sep. 9, 1988, now abandoned.

This invention relates to a cosmetic preparation having germicidal properties and the use of 5-hydroxy-1,4-naphthoquinone as a germicidal agent for cosmetic preparations.

This invention relates to a cosmetic preparation which is to be understood as such not in the presently legal sense but in the sense of application and has gained germicidal or germ-inhibiting properties by the addition of 5-hydroxy-1,4-naphthoquinone.

The expression of "cosmetic preparation" used in the present application comprises cosmetic agents, cosmetics and preparations for body care.

Dental caries is known to be the presently most frequent civilizational disease, from which more than 90% of the population living in industrial countries suffer. In spite of all efforts made to influence the genesis of this disease by means of effective preparations, a lasting and striking success is presently not observed. Up to now, fluoride additions to preparations for dental care or drinking water have proved to be most effective because they harden the tooth surfaces and make them more resistant to the organic acids formed by the bacterial population of the plaque. According to the present state of the art the direct and most effective influence on caries genesis, i.e. killing the acid-forming plaque mixed population, is certainly only possible by means of antibiotics whose permanent use which would be required for this purpose is known to be extremely problematic for reasons of resistance developing.

In North Africa it was observed that a considerably poorer part of certain groups of the population, above all those living in the Atlas Mountains, chewed dried plant parts of JUGLANS REGIA for the purpose of dental care. These people distinguish themselves by a remarkably good condition of their teeth.

In European industrial countries, the use of dried JUGLANS REGIA corresponding to that in North Africa is not possible in this form for reasons of taste and esthetics.

According to the state of the art chemically complex, synthetic, germicidal substances are used in deodorizing cosmetic products, e.g. in a deodorant gel in amounts of about 5,000 mg/kg. However, it can be observed that a measurable part of the population may develop allergic reactions to these synthetic substances. Moreover, a major, still increasing part of the population rejects what is called "artificial" substances in consumers' goods whatever the reasons are and prefers "natural" substances having corresponding effects.

The object of the present invention is to provide a cosmetic preparation having germicidal properties, which contains a tolerable germicidal agent in low concentration and not a chemically complex, synthetic substance as the germicidal agent. The cosmetic preparation is to be easily tolerable and contain a natural substance as the germicidal agent.

According to the invention especially a storageable formulation to which the North and Central Europeans are used is to be provided for anti-carious preparations for dental care. According to the invention deodorizing cosmetic products are to be provided, which have germicidal properties and do not contain a chemically complex, synthetic germicidal agent.

According to the invention cosmetic preparations are to be provided, especially preparations for dental and oral care, which contain plant parts of JUGLANDACEAE species as the germicidal agent.

The subject matter of the invention is a cosmetic preparation having germicidal properties which is characterized in that it contains 5-hydroxy-1,4-naphthoquinone. The cosmetic preparation according to the invention preferably contains the 5-hydroxy-1,4-naphthoquinone in the form of plant parts having a content of 5-hydroxy-1,4-naphthoquinone or in the form of an extract, the extract being obtained by extraction from plants having a content of 5-hydroxy-1,4-naphthoquinone. The plant parts preferably come from JUGLANDACEAE species.

Furthermore, the invention relates to the use of 5-hydroxy-1,4-naphthoquinone as the germicidal agent for cosmetic preparations, the 5-hydroxy-1,4-naphthoquinone being preferably used in the form of plant parts having a content of 5-hydroxy-1,4-naphthoquinone or in the form of an extract, the extract being obtained by extraction from plants having a content of 5-hydroxy-1,4-naphthoquinone.

A more detailed investigation showed that the main active substance of JUGLANDACEAE species, the 5-hydroxy-1,4-naphthoquinone which is also referred to as JUGLONE, of the following formula I is:

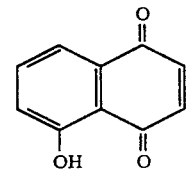

The investigations showed that the 5-hydroxy-1,4-naphthoquinone is unstable to certain external influences and tends to form condensation products as is generally common with quinones.

It was found surprisingly that the condensation reaction of the naphthoquinone derivative, which takes place in vitro together with an increasing decrease of the germicidal effect, can be suppressed and/or delayed when a small amount of this compound is admixed to cosmetic products. Particularly, it turned out that the condensation reaction can be suppressed and/or delayed in the dried JUGLANDACEAE drug when the moisture content of the dried plant or plant parts was lowered to at most 0.3 to 0.5%. From a health point of view, the harmlessness of the compound of formula I as well as the use of JUGLANDACEAE plants or plant parts might be considered proven by the use in North Africa probably lasting for centuries. Indeed, the 5-hydroxy-1,4-naphthoquinone, i.e. the active substance of JUGLANS REGIA, is not unphysiological. Many substances belonging to the group of substituted naphthoquinones have a vitamin K efficacy. Vitamin $K_1$ is also a substituted naphthoquinone. Moreover, extracts from JUGLANS REGIA have long been used as what is called typagen for coloring alcoholic beverages.

According to the invention the 5-hydroxy-1,4-naphthoquinone may be used as such or JUGLANDACEAE species may be used. The JUGLANDACEAE species used may be the species indicated in "Taschenbuch der Drogenkunde" by Heinz A. Hoppe, Walter de Gruyter, Berlin, N.Y., 1981, pages 155 to 156. According to the invention it is particularly preferable to use JUGLANS REGIA L. and JUGLANS NIGRA L. According to the invention the entire plants may be used in comminuted, preferably ground, form or plant parts may be used.

Plant parts containing 5-hydroxy-1,4-naphthoquinone are also to comprise those plant parts containing the biological precursors compound such as, for example, α- and β-hydrojuglone, a glucoside which, among others, can also be decomposed by ferments thereby forming juglone. According to the invention leaves, fruit peels, nuts, dried fruit peels and the barks (CORTEX) may be used. According to the invention comminuted or ground root barks are preferably used.

As stated above, it is preferred to reduce the water content of the dried plant to 1.0%, preferably to a value within the range of from 0.3 to 0.5%. According to the invention it is particularly preferred to treat, preferably spray, the ground dried drug with a hydrophobing substance before using it. According to the invention the ground, dried plant parts of JUGLANDACEAE species, preferably JUGLANS REGIA, are sprayed in known manner with 0.5 to 2.0%, preferably 0.5 to 1.0%, of a hydrophobing agent. Suitable hydrophobing agents are the known water-repellent liquids. It is particularly preferred to use silicone fluid. Examples are fatty oils (glyceryl ester of fatty acids), paraffin oils and other water-repellent substances. Rendering JUGLANS plant parts hydrophobic by the hydrophobing substance can be carried out, for example, by soaking the plant parts or by spraying. According to the invention the plant parts of the JUGLANDACEAE species may also be extracted, and the resulting extract can then be added to the basic composition of the cosmetic preparation. According to the invention the above-mentioned dried plant parts of JUGLANDACEAE species are extracted in comminuted form, preferably as a powder, with an extracting agent consisting of 70 to 100% of ethanol and 0 to 30% of water.

The inventive alcoholic extract of the dried drug is prepared by mixing e.g. 100 g of dried, ground JUGLANS REGIA plant parts and 1000 ml of ethanol, containing 0 to 30% by volume, preferably 10 to 25% by volume, particularly preferably 15% by volume, of water, in that this mixture is set aside in the absence of light at room temperature for 12 to 24 hours by stirring from time to time. Then, it is filtered and the extract is stored in a dark and cool place.

After adding it to certain cosmetic preparations an extract prepared with pure water or pure ethanol as the extracting agent surprisingly led to unsatisfactory results in the agar diffusion test, i.e. no or only small inhibiting zones resulted. Surprisingly, it showed that an extracting agent consisting of 70 to 90% of ethanol and 10 to 30% of water yielded an extract effective when used in cosmetic preparations. In the agar diffusion test these cosmetic preparations showed surprisingly large inhibiting zones in plaque mixed cultures and mixed cultures from the armpit on total count culture media.

Even after several months, the extract prepared according to the invention is equally effective when stored in a dark and cool place.

Surprisingly it showed that only very small amounts of 5-hydroxy-1,4-naphthoquinone are required. If pure 5-hydroxy-1,4-naphthoquinone is used it is preferably added to the cosmetic preparation as an alcohol solution or aqueous alcohol solution. It is used such that the cosmetic preparation contains 0.001 to 0.5% by weight, preferably 0.005 to 0.1% by weight, of 5-hydroxy-1,4-naphthoquinone, based on the water content of the substrate. When producing the cosmetic preparations according to the invention only very small amounts of dried plants or extract are required to obtain the desired effects. The plant parts or the extract is added to the cosmetic preparation in amounts such that the content of 5-hydroxy-1,4-naphthoquinone is 0.001 to 0.5% by weight, based on the water content of the substrate.

For producing an anti-carious chewing gum e.g. 0.5 to 10% of dried JUGLANS REGIA plant parts rendered hydrophobic according to the invention or plant parts not rendered hydrophobic are admixed to a known gum composition and processed according to known processes to give the finished product.

10 to 100% by volume of the pure inventive extract flavored with essential oils are used for an anti-carious mouthwash usually diluted with very much water when used, so that the juglone content in the mouthwash is from 0.1 to 5.0%.

As the active substance deodorizing products contain 0.1 to 10% of dried and ground JUGLANS REGIA plant parts rendered hydrophobic or — depending on the formulation of the finished product — 1 to 100% of extract according to the invention, based on the total product.

Cosmetic preparations according to the invention are hygienic articles such as soaps, preparations for feminine hygiene, for hair, head, oral and dental care, deodorants as well as cosmetic products for care and beauty, sunscreen agents, skin preparations, face packs and the like. The basic compositions of the preparations known as such are not to be dealt with in detail. According to the invention a small amount of 5-hydroxy-1,4-naphthoquinone or plant parts of JUGLANDACEAE species or an extract from plant parts of JUGLANDACEAE species is added to these preparations. Preferable cosmetic preparations according to the invention are preparations for dental care serving the purpose of caries prophylaxis and deodorants, since a relatively small dose has a maximum germicidal effect. According to the invention particularly chewing gum for dental care, toothpastes, a tooth powder or a mouthwash as well as deodorants and foot powders are preferred.

Using the powdered and dried plant material stabilized by rendering hydrophobic and/or an extract having water-containing ethanol permits the production of a plurality of cosmetic preparations such as toothpastes, chewing gum for dental care, tooth powders, mouthwash-deodorant products, foot powders and so on. These products are particularly preferred.

As was proven in vitro in the agar diffusion test, the products for dental care according to the invention are particularly effective against the bacterial population of tooth plaque and the cosmetic deodorizing products according to the invention are particularly effective against the mixed population of the body surface, which causes the unpleasant smells of the body surface.

In the agar diffusion test and other in vitro experiments a surprisingly high efficacy of both dried and ground drug and extract from the drug could unexpectedly be detected. After inoculating a culture medium with a plaque mixed culture a piece of dried JUGLANS REGIA having a weight of 100 mg resulted in the agar diffusion test in an inhibiting zone of 35 mm in diameter subsequent to incubation. After inoculation of the culture medium with a mixed culture from the armpit an inhibiting zone having a diameter of 38 mm resulted under the same conditions. In a submersion culture it showed that merely 1000 mg of dried and finely ground JUGLANS REGIA in 1 kg of substrate were sufficient to kill all of the germs of the previously inoculated substrate. The same effect was obtained when only 32.5 mg of juglone were admixed.

As compared with the costs for synthetic conventional bactericidal active substances to be used in substantially higher concentrations, those ones for the ground dried JUGLANS REGIA drug are to be considered very low.

Example of using a pure active substance from JUGLANS REGIA (JUGLONE):

A piece of cellulose felt having a thickness of about 2 mm and an area of 5×5 mm was soaked with 0.1 ml of a 0.25% JUGLONE solution in alcohol and dried in the presence of air. This piece of cellulose felt prepared in such a way was applied to a total count culture medium previously inoculated over its entire surface (90 mm in diameter) with the following mixed populations:
1. tooth plaque population
2. armpit population
3. saccharomyces cerevisiae (pH 7)
4. saccharomyces cerevisiae (pH 3.4).

The inhibiting zones developing after incubation at 25° C. for about 18 hours had the following diameters:
1:30 mm
2:46 mm
3:30 mm
4:56 mm.

The following examples explain the invention.

EXAMPLE 1

Composition example of a chewing gum:

In a special kneader 10 to 80 g of finely ground dried plant materials of e.g. JUGLANS REGIA root bark are thoroughly admixed to 1 kg of a known gum mixture in the production step in which the flavor is added. Care must be taken that soon after the addition of the JUGLANS powder the composition is cooled as specified in the process.

Mixture example:
15 to 25% of gum base
20 to 30% of glucose syrup
50 to 60% of powdered sugar
0.5 to 8% of dried JUGLANS powder
1 to 2% of conventional plasticizer (e.g. glycerol)
3 to 6% of residue water content.

For "sugar-free" compositions the glucose syrup and the powdered sugar may be be replaced by the sugar alcohols mannitol, xylitol and sorbitol, "palatinit" and others as well as artificial sweeteners such as saccharin, cyclamate, acesulfam K and aspartame.

This composition only represents an example. Throughout the world the practice of gum formulation has brought about diverse modifications therefrom, all of which however correspond approximately to the above composition.

In order to increase the durability of the JUGLANS substance the JUGLANS powder may be treated according to the invention with a hydrophobing substance before being admixed.

The above-described admixture of JUGLANS powder approximately corresponds to a 5-hydroxy-1,4-naphthoquinone content of 16 to 260 mg per 100 g finished chewing gum mixture. In this concentration the 5-hydroxy-1,4-naphthoquinone may also be admixed as a pure substance instead of the JUGLANS powder to obtain the same effect.

EXAMPLE 2

Composition example of a deodorant gel applied with a "roll-on deodorant":

100 ml of a basically known deodorant gel composition are composed of:
1 to 100 ml of an ethanol-water extract from fresh or dried JUGLANS REGIA root bark,
0 to 99 ml of ethanol-water mixture,
0.1 to 10% of methyl cellulose or polyoxyethylene polyoxypropylene block polymer
sufficient quantity of perfume oil.

Other technically or chemically required additives may be added. Instead of the extract from JUGLANS bark an ethanolic-aqueous solution of 5-hydroxy-1,4-naphthoquinone with a total of 16 to 260 mg of active substance per 100 ml of deodorant gel may be used by obtaining the same effect. Other suitable solvents may also be used in place of the ethanol.

EXAMPLE 3

Composition example of a foot powder:

100 g of a basically known foot powder are composed of:

| | |
|---|---|
| talc | 70.0 g |
| magnesium hydroxyde carbonate | 19.2 to 29.1 g |
| allantoin | 0.5 g |
| perfume oil | 0.3 g |
| JUGLANS root bark powder | 0.1 to 10 g. |

Instead of the JUGLANS root bark powder a mixture of 3.25 mg to 400 mg of 5-hydroxy-1,4-naphthoquinone with a suitable carrier substance, e.g. talc, may be used by obtaining the same effect.

I claim:

1. A germicidal chewing gum, deodorant gel or foot powder composition, comprising 5-hydroxy-1,4-naphthoquinone in the form of plant parts containing 5-hydroxy-1,4-naphthoquinone, wherein the plant parts are root barks, the 5-hydroxy-1,4-naphthoquinone is present in an extract or a finely ground form and the 5-hydroxy-1,4-naphthoquinone is present in an amount between about 0.001 and 0.5% by weight.

2. The composition according to claim 1, wherein the 5-hydroxy-1,4-naphthoquinone is in the form of an extract, the extract being obtained by extraction from root barks containing 5-hydroxy-1,4-napthoquinone.

3. The composition according to claim 1, wherein the root barks are of the JUGLANDACEAE species.

4. The composition according to claim 3, wherein the root barks are present in finely ground form.

5. The composition according to claim 3, wherein the root barks are selected from the group consisting of JUGLANS REGIA L. and JUGLANS NIGRA L.

6. The composition according to claim 1, further comprising a hydrophobic substance, the root barks being treated with the hydrophobic substance.

7. A process for the production of the chewing gum, deodorant gel or foot powder composition of claim 1, wherein 5-hydroxy-1,4-naphthoquinone, root barks containing 5-hydroxy-1,4-naphthoquinone, or an extract obtained therefrom is admixed with a basic composition of the chewing gum, deodorant gel or foot powder composition.

8. A method of disinfecting a body surface comprising the step of applying to the body surface a germicidal chewing gum, deodorant gel or foot powder composition comprising 5-hydroxy-1,4-napthoquinone in the form of plant parts containing 5-hydroxy-1,4-naphthoquinone, wherein the plant parts are root barks and the 5-hydroxy-1,4-naphthoquinone is present in an amount between about 0.001 and 0.5% by weight.

9. The method according to claim 8, wherein 5-hydroxy-1,4-naphthoquinone is in the form of an extract, the extract being obtained by extraction from root barks containing 5-hydroxy-1,4-naphthoquinone.

10. The method according to claim 8, wherein said root barks are of the JUGLANDACEAE species.

11. The method according to claim 10, wherein the root barks of the JUGLANDACEAE species are present in finely ground form.

12. The method according to claim 10, wherein the JUGLANDACEAE species are selected from the group consisting of JUGLANS REGIA L. and JUGLANS NIGRA L.

13. The method according to claim 8, further comprising a hydrophobic substance, the root barks being treated with the hydrophobic substance.

* * * * *